(12) United States Patent
Mougin et al.

(10) Patent No.: US 6,395,265 B1
(45) Date of Patent: May 28, 2002

(54) COSMETIC COMPOSITIONS CONTAINING MULTI-BLOCK IONIZABLE POLYSILOXANE/POLYURETHANE AND/OR POLYUREA POLYCONDENSATES IN SOLUTION, AND USES THEREOF

(75) Inventors: Nathalie Mougin, Paris; Jean Mondet, Aulnay-sous-Bois, both of (FR)

(73) Assignee: L'Oreal (FR)

(*) Notice: Subject to any disclaimer, the term of this patent is extended or adjusted under 35 U.S.C. 154(b) by 0 days.

(21) Appl. No.: 08/913,061

(22) PCT Filed: Dec. 10, 1996

(86) PCT No.: PCT/FR96/01976

§ 371 (c)(1),
(2), (4) Date: Sep. 5, 1997

(87) PCT Pub. No.: WO97/25021

PCT Pub. Date: Jul. 17, 1997

(30) Foreign Application Priority Data

Jan. 5, 1996 (FR) .............................................. 96 00098

(51) Int. Cl.⁷ ........................ A61K 7/075; A61K 7/043; A61K 7/032; A61K 47/34
(52) U.S. Cl. ........................ 424/70.12; 424/61; 424/69; 525/452
(58) Field of Search ............................... 424/401, 78.18, 424/70.12, 70.17, 59, 61, 63, 69, DIG. 2, DIG. 1; 525/452, 474; 514/772.1; 510/122

(56) References Cited

U.S. PATENT DOCUMENTS

| 4,092,275 A | * | 5/1978 | Reischl et al. |
| 4,518,758 A | * | 5/1985 | Cavezzan et al. |
| 4,767,826 A | * | 8/1988 | Liang et al. |
| 4,935,482 A | * | 6/1990 | Decker et al. |
| 4,962,178 A | * | 10/1990 | Harisiades |
| 5,221,724 A | * | 6/1993 | Li et al. |
| 5,290,615 A | * | 3/1994 | Tushaus et al. |
| 5,643,581 A | | 7/1997 | Mougin et al. |

OTHER PUBLICATIONS

Otsuki et al, polymer Journal 24(4) pp 347–355, 1992.*

* cited by examiner

Primary Examiner—Edward J. Webman
(74) Attorney, Agent, or Firm—Finnegan, Henderson, Farabow, Garrett, & Dunner, L.L.P.

(57) ABSTRACT

Cosmetic compositions based on multiblock ionizable polycondensates, and uses thereof The invention relates to novel cosmetic or dermatological compositions, characterized in that they comprise, in a cosmetically acceptable support, at least one solution or one emulsion of at least one multiblock polycondensate whose chain consists of the repetition of at least one polysiloxane block and of at least one polyurethane and/or polyurea block; the said polyurethane and/or polyurea block also including ionizable groups and the said polycondensate being dissolved in an aqueous, organic or aqueous-organic solvent system. These compositions may be used in particular in the cosmetic field of hair care, make-up or skincare.

54 Claims, No Drawings

COSMETIC COMPOSITIONS CONTAINING MULTI-BLOCK IONIZABLE POLYSILOXANE/POLYURETHANE AND/OR POLYUREA POLYCONDENSATES IN SOLUTION, AND USES THEREOF

This application is a 371 of PCT/FR96/01976 filed Dec. 10, 1996.

The present invention relates to novel cosmetic or dermatological compositions with film-forming properties, containing solutions of specific multiblock ionizable polycondensates, as well as to various possible uses thereof, in particular in the field of cosmetic (i.e. topical) treatment of the skin, the hair, the nails and other keratin substances.

It is common practice in cosmetic formulations, in particular in hair products (shampoos, conditioners, styling or treating lotions or gels, lacquers or lotions for shaping, setting, fixing, and the like the hair) or in make-up products (such as, for example, nail varnish, mascaras, eyeliners and the like), to use a variable proportion, depending on the nature and destination of the formulation, of at least one film-forming substance which makes it possible, or is intended to give the support on which it is applied (that is to say, here, one of the surface parts of the body, such as head hair, eyelashes, body hair, skin, nails, etc.) certain improved characteristics. Thus, for example, in the specific case of treating a head of hair, more staying power and more softness of the hair are especially sought by this technique, whereas in the more specific case of the nails, it is mainly sought to obtain a protective, shiny and hard film which adheres fully to the nails.

In order to be satisfactory in cosmetic applications, a film-forming resin needs to have certain restricting characteristics or properties, among which mention may be made more particularly, in a non-limiting manner, firstly, of a very good affinity/compatibility/harmlessness with respect to various keratin substances (skin, hair and the like), next, good film-forming properties relative to these substances (quality and uniformity of the film deposited), and, lastly, good remanence properties (adhesiveness, solidity), that is to say that it must be difficult to remove from its support by simple washing with water or using detergents (shampoos) for example. In the case of nail varnishes, the film must also have good mechanical abrasion strength. In general, it will be noted that it is often difficult in practice to find a film-forming substance which is capable of effectively satisfying several, or all, of the various cosmetic applications which may be envisaged for this substance (problem of the acceptable compromise).

In certain respects, the film-forming substances known to date, and in particular those mentioned above, are poorly suitable for obtaining compositions having good cosmetic properties, on account, in particular, of an appreciable lack of remanence, in particular of water-resistance.

Another problem lies in the fact that the films thus obtained, in particular in the context of applications of mascara or hair type, are not sufficiently shiny. This sheen is also only poorly remanent, that is to say that it disappears quickly under the action of external agents (highly water-sensitive in particular).

However, the sheen, as well as the remanence of this sheen, nowadays constitutes a particularly desired property in the field of cosmetics.

It is thus seen that there is currently a strong need in the state of the art to have available cumulating film-forming compositions, for a varied field of possible applications (hair, eyelashes, skin, nails, etc.), all the advantages generally desired or desirable in cosmetics, namely, in particular, harmlessness towards keratin substances, ease of application and of use, production of thin and uniform protective deposits, remanence of the adhesive properties, provision and remanence of sheen properties, provision of softness and lubrication, rigidity and abrasion-resistance.

In order to meet this need, it has been proposed to use mixtures of polymers which make it possible to combine all of these properties, in particular mixtures of polyorganosiloxanes (silicones) with non-silicone polymers. The reason for this is that it is known that silicones provide excellent surface properties, leading to good lubrication, good sheen and a soft feel without providing fatty substances. These polymers do not have good mechanical properties for ensuring good film-formation; they thus need to be combined with other polymers which provide mechanical properties. Polyorganopolysiloxanes, in particular polydimethylsiloxanes, are incompatible with most of the non-silicone polymers which provide mechanical properties.

To overcome these drawbacks, French patent No. 2,708, 199 teaches the possibility of using a stable aqueous suspension consisting of fine, solid, generally spherical particles of polysiloxane/polyurethane and/or polyurea multiblock ionic polycondensate, these particles having been obtained by placing the said polycondensate in the pre-synthesized state in dispersion in a suitable aqueous phase. This type of dispersion of water-insoluble polymer is called a "pseudo-latex". However, these pseudo-latices have certain drawbacks.

These ionizable polycondensates in aqueous suspension do not make it possible to potentiate the desired conjugation of the properties provided, on the one hand, by the silicone segments and, on the other hand, by the polyurethane and/or polyurea segments. This additivity of the properties can only be optimized if good phase separation between the silicone segments and the polyurethane and/or polyurea segments takes place during drying, such that there is, on the one hand, in the solid state, an actual stratification of the silicone segments at the surface of the matrix of the deposit consisting of the polyurethane and/or polyurea segments—it is, in fact, at the interface of this matrix with air that the specific properties of the silicones will be manifested—and, on the other hand, such that the silicone segments are assembled inside the matrix of the deposit in the form of a dispersed phase.

It is very difficult to obtain, with pseudo-latices consisting of polysiloxane/polyurethane and/or polyurea ionizable polycondensates, good phase separation leading to this stratification of the silicone segments at the surface of the deposit and the formation of a silicone phase inside the deposit, and more particularly when the lengths of the polysiloxane and/or polyurethane and/or polyurea sequences are short. The result of this is that the additivity of the properties as defined above which is obtained by these pseudo-latices still remains insufficient.

Thus, after considerable research conducted in this matter, the Applicant has now found, surprisingly and unexpectedly, that it is possible to improve this phase separation substantially and consequently to potentiate the additivity of the surface properties provided by the silicones and the mechanical and/or adhesion properties provided by the polyurethanes and/or polyureas, by using solutions or emulsions of these same polysiloxane/polyurethane and/or polyurea multiblock ionizable polycondensates dissolved in an aqueous, organic or aqueous-organic solvent system.

Furthermore, the polycondensates in solution of the invention exhibit better remanence of the deposit to the action of water or of surfactant solutions (shampoos) than pseudo-latices consisting of the same polycondensates.

In accordance with the present invention, novel cosmetic compositions are therefore now proposed, which are characterized in that they comprise, in a cosmetically acceptable support, at least one solution or one emulsion of at least one multiblock polycondensate whose chain consists of the repetition of at least one polysiloxane block and of at least one polyurethane and/or polyurea block; the said polyurethane and/or polyurea block also including ionizable groups and the said polycondensate being dissolved in an aqueous, organic or aqueous-organic solvent system.

The expression "ionizable group" is understood to refer to any group which may be ionized by a neutralization reaction of an acidic or basic function borne by the said group, or a quaternization reaction of a tertiary amine function borne by the said group, and which may thus form an anionic, cationic, amphoteric or zwitterionic group.

The polycondensates of the invention are essentially prepared according to a two-step process. The first step consists of a standard polycondensation reaction between (i) a polysiloxane (or silicone) polymer having a hydroxyl function or an amine function at the ends of its chain (i.e. an α,ω-dihydroxypoly-siloxane, or an α,ω-diaminopolysiloxane, or an α,ω-aminohydroxy- or hydroxyamino-polysiloxane), and (ii) a diisocyanate (present in stoichiometric amount, or in stoichiometric excess, that is to say at more than 2 mol per mole of silicone), whereby a novel silicone is obtained, this time having an isocyanate function at each of its chain ends; then, in a second step, the chains of the polycondensate obtained above are coupled by means of a coupling agent (in variable amount chosen as a function of the desired final chain length) chosen from diols and/or diamines and/or alcoholamines, so as finally to obtain a novel polycondensate of longer chain length.

The reactions used in the first step thus lead to a polysiloxane having at its chain ends, besides the isocyanate functions mentioned above, urethane and/or urea units, according to the standard mechanisms for a condensation reaction carried out between (i) an isocyanate function, as borne by the starting diisocyanate, and (ii) an alcohol function (creation of a urethane unit in this case) or of an amine function (formation of a urea function in this case), as borne by the starting polysiloxane, namely:

(polysiloxane)-OH+O=C=N—R—N=C=O→-(polysiloxane)-O—CO—NH—R—N=C=O (diisocyanate)

and/or (polysiloxane)-NH2+O=C=N—R—N=C=O→-(polysiloxane)-NH—CO—NH—R—N=C=O

The polycondensates obtained after this first step may thus effectively be defined by the general formula (1) below:

O=C=N—R—NH—CO=X¹-(polysiloxane)-X¹—O—NH—R—N=C=O     (1)

in which X¹ may thus represent, separately or in combination, —O— or —NH—.

In the second step, the alcohol and/or amine functions of the coupler (which coupler may conveniently be symbolized here by OH—B—OH, or NH₂—B—NH₂ or alternatively NH₂—B—OH) then react, according to the same mechanisms as those shown for the first step, either with the isocyanate functions borne at the end of the chain by the polysiloxane polycondensate of formula (1) above, or with isocyanate functions borne by free diisocyanate, when the latter has been introduced in stoichiometric excess during the first step, thus giving rise in the chain (longer) of the new polycondensate obtained to a sequence of urethane and/or urea units, that is to say polyurethane and/or polyurea type blocks which may be symbolized by formula (2):

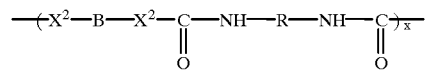

which X² represents —O— or —NH—, and x is a value corresponding substantially to the number of moles of coupler used in the reaction.

As indicated above, a polycondensate consisting of the repetition of polysiloxane blocks (corresponding simply to the starting polysiloxane, and as appears in formula (1)) and polyurethane and/or polyurea blocks (formula (2)) is thus finally obtained.

According to an extremely important aspect of the invention, the couplers (that is to say, effectively, the radical B) bear ionizable groups, that is to say groups which, and respectively, when subjected to the action of a base, give anionic groups (this is the case, for example, of carboxyl groups) and when subjected to the action of an acid or quaternization, give cationic groups (the case, for example, of a tertiary amine). Neutralization of the anionizable groups (or cationizable groups respectively) with the base (or the acid respectively) may be carried out partially or completely, depending on the amounts of neutralizing agents used.

However, other characteristics, aspects and advantages of the invention will now become more apparent on reading the detailed and full description which follows, as well as the various concrete, but in no way limiting, examples intended to illustrate it.

As indicated above, the chain of the ionizable polycondensate used in the context of the present invention is essentially characterized in that it consists of the repetition (or alternation) of at least one polysiloxane type block and of at least one polyurethane and/or polyurea type block, the said polyurethane and/or polyurea blocks containing ionizable groups. Other blocks of different chemical nature may be in the chain of the polycondensate. Mention may be made, for example, of polyether blocks such as polyoxyethylene, polyoxypropylene, polytetramethylene oxide and/or polyester blocks such as poly(ethylene glycol adipate), poly(neopentyl glycol sebacate) or poly(ethylene glycol terephthalate).

The repetition of the above blocks may be of random type, but it is preferably of regularly alternating type. In addition, the numerical ratio between the polyurethane and/or polyurea type blocks and the polysiloxane type blocks is generally between 1 and 10, preferably between 1 and 3.

The molecular weights of the polysiloxane-polyurethane/polyurea polycondensates may vary within a wide range, in particular between 2000 and 500,000, but preferably between 3000 and 250,000.

Preferably, the polysiloxane block corresponds to the general formula (I) below:

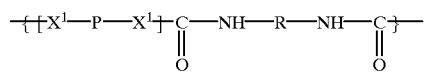

which: in

P is a polysiloxane segment, $X^1$ represents, separately or in combination, —O— or —NH—, and R (which is none other than the diisocyanate unit as mentioned above) is a divalent radical chosen from alkylene radicals of aromatic, aliphatic or cycloaliphatic type.

Preferably, the polysiloxane segment P corresponds to the general formula (I') below:

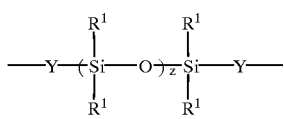

(I')

which the Radicals $R^1$, which may be identical or different, are chosen, on the one hand, from monovalent $C_1$–$C_{20}$ hydrocarbon radicals which are free or substantially free of ethylenic unsaturations, and, on the other hand, aromatic radicals, Y represents a divalent hydrocarbon radical and z is an integer such that the average molecular weight of the polysiloxane segment is between 300 and 10,000.

Preferably, Y is a divalent radical chosen from alkylene radicals of formula —$(CH_2)_a$—, in which a represents an integer which may be between 1 and 10.

As radicals $R^1$ which are suitable in the context of the invention, mention may be made more particularly of alkyl radicals and, in particular, methyl, ethyl, propyl, isopropyl, butyl, pentyl, hexyl, octyl, decyl, dodecyl and octadecyl radicals, cycloalkyl radicals, in particular the cyclohexyl radical, aryl radicals, in particular phenyl and naphthyl, arylalkyl radicals, in particular benzyl and phenylethyl, and tolyl and xylyl radicals. It will be noted that, according to the invention, it is important for the polysiloxane segment to be free, or substantially free, of units of the Si—H or Si—$R^1$ type in which $R^1$ represents a hydrocarbon radical having ethylenic unsaturations, so as to avoid any untimely crosslinking of the polycondensate with itself.

According to a particularly preferred embodiment of the present invention, the polysiloxane segment P present in the polycondensates corresponds to formula (I″) below:

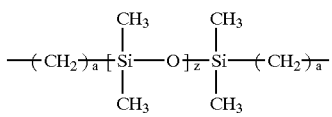

(I″)

in which a and z are values as defined above.

As regards, now, the polyurethane and/or polyurea blocks which form a part of the polycondensates used in the context of the invention, these preferably correspond to the general formula (II) below:

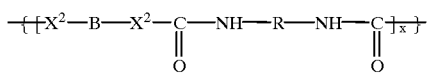

which: in $X^2$ represents, separately or in combination, —O— or —NH—,

R (which, as above for formula (I), is none other than the diisocyanate unit used to carry out the condensation reaction) is as defined above for the blocks of formula (I), x (which, as indicated above in the description corresponds substantially to the number of moles of couplers used in the process for synthesizing the polycondensate) is an integer which may range from 1 to 10 and preferably from 1 to 3, and B (which is none other than the unit provided by the coupler as mentioned above) is a divalent hydrocarbon radical bearing a positive or negative ionic charge.

As radicals B bearing anionic groups (i.e. negative charges), mention may be made more particularly of those which bear groups having one or more carboxylic function (s) and/or one or more sulphonic functions, the said carboxylic and/or sulphonic functions being in free form or being partially or totally neutralized with an inorganic or organic base, as will be explained in greater detail hereinbelow.

Thus, among the divalent radicals B bearing carboxylic or sulphonic functions which are particularly suitable in the context of the present invention, mention may be made of those of formula (III):

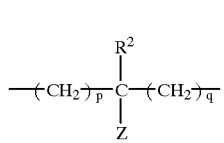

(III)

which $R^2$ represents a linear or branched $C_1$–$C_3$ alkyl radical, Z represents a carboxylic acid (—COOH) function or sulphonic acid (—$SO_3H$) function or a salt of the said acidic functions (carboxylate and sulphonate functions, respectively), and p and q, which may be identical or different, are integers between 1 and 5, and those of formula (III'):

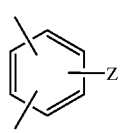

(III')

in which z has the above meaning.

As radicals B bearing cationic groups (i.e. positive charges), mention may be made more particularly of those which bear groups of tertiary amine type, the said tertiary amines being either non-neutralized or partly or totally neutralized (presence of —$NH^+$— units) or quaternized, as will be explained in greater detail hereinbelow.

Thus, among the divalent radicals B bearing cationizable tertiary amine functions which are particularly suitable in the context of the present invention, mention may be made of those of formula:

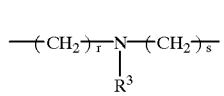

(IV)

which $R^3$ represents a linear or branched $C_1$–$C_4$ alkyl radical and r and s are both integers, which may be identical or different, which may be between 1 and 10.

In neutralized or quaternized form, the above radicals B then become:

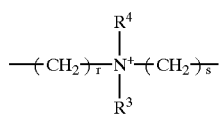
(IV')

in which formula $R^3$ has the above meaning, and $R^4$ represents either hydrogen (neutralization) or a linear or branched $C_1$-$C_{10}$ alkyl radical or an aromatic ring (quaternization).

According to the invention, the degrees of neutralization of the anionizable or cationizable functions may be between 0 and 100%, preferably between 10 and 100%.

The radicals B of the coupler bearing an ionic charge may be used alone or as a mixture with other radicals B' originating from couplers not bearing an ionizable group.

Lastly, as regards the radicals R more particularly preferred according to the present invention, which fall within the scope of the definition of the blocks of formulae (I) and (II) given above, mention may be made of those of formulae:

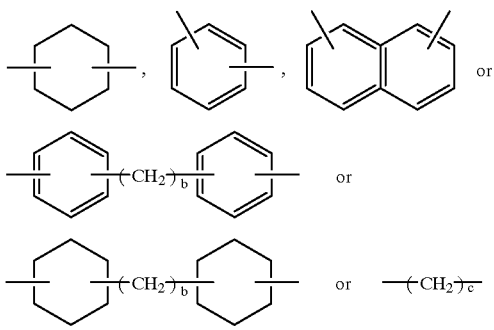

which b is an integer between 0 and 3 and c is an integer between 1 and 20, preferably between 2 and 12.

Among the particularly preferred divalent radicals R which fall within the scope of the above formulae, mention may be made of hexamethylene, 4,4'-biphenylenemethane, 2,4- and/or 2,6-tolylene, 1,5-naphthylene, p-phenylene and methylene-4,4-bis-cyclohexyl radicals and the divalent radical derived from isophorone.

The process for synthesizing the polycondensates used in the context of the present invention will now be developed in slightly more detail. In these main points, this process corresponds to that already indicated at the start of the description.

An α,ω-dihydroxy and/or diamino and/or amino-hydroxy and/or hydroxyaminopolysiloxane corresponding to the following general formula:

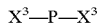
$X^3$—P—$X^3$ in which P has the meaning given above (polysiloxane segment) and $X^3$ represents, in combination or separately, —OH or —NH$_2$, is reacted, in an organic solvent, with a stoichiometric excess of a diisocyanate of formula:

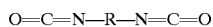
O=C=N—R—N=C=O in which R has the meaning given above, followed by coupling the chains of the polycondensate obtained above with at least one diol and/or a diamine and/or an aminoalcohol corresponding to the formula:

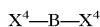
$X^4$—B—$X^4$ in which B has the meaning given above and $X^4$ represents —OH or —NH$_2$, at a temperature of between 40 and 100° C., in the presence of a tin salt as catalyst. This diol and/or this diamine $X^4$—B—$X^4$ may be used alone or as a mixture with one or more diols or diamines or amino alcohols not containing ionizable groups, for example 1,4-butanediol.

The organic solvent used in these steps is preferably chosen from the group consisting of acetone, methyl ethyl ketone, tetrahydrofuran and 1,2-dichloroethane, the solvents being inert towards isocyanate groups.

The tin salt is, itself, preferably chosen from 2-ethyltin hexanoate and dibutyltin dilaurate.

In the context of carrying out the above process, the diisocyanates which are particularly preferred are chosen, alone or as mixtures, from diphenylmethane 4,4'-diisocyanate and methylene-4,4'-dicyclohexyl diisocyanate, and the couplers which are particularly preferred are chosen, alone or as mixtures, from dimethylolpropionic acid, N-methyldiethanolamine, 1,3-diaminopropane and ethanolamine, it being understood that the possibility of mixing acidic coupler/amino coupler is excluded.

The polysiloxane-polyurethane/polyurea polycondensate thus obtained may then optionally be purified, for example by precipitation in a non-polar solvent such as cyclohexane.

In accordance with the invention, this optionally purified polycondensate is then either used in its natural state or neutralized using a suitable neutralizing agent which may be either an inorganic or organic base when the radical B as defined above bears anionizable functions such as, for example, carboxylic and/or sulphonic acid functions, or an inorganic or organic acid when the said radical B bears cationizable functions such as, for example, tertiary amine functions; or quaternized using an alkyl halide, an acidic salt bearing a labile halogen or a sultone (for example propane sultone) when the said radical B bears tertiary amine functions.

According to the invention, the degree of neutralization may range from 0% to 100%, preferably from 10% to 100%.

It goes without saying that the nature of the neutralizing agent which will be suitable for use in neutralizing the polysiloxane-polyurethane/polyurea polycondensate will depend on the nature of the ionizable functions borne by this polycondensate.

When the said polycondensate contains an anionizable function such as, for example, a carboxylic or sulphonic acid function, the neutralizing agent may be an inorganic base such as sodium hydroxide, potassium hydroxide or aqueous ammonia, or an organic base such as an amino alcohol chosen in particular from 2-amino-2-methyl-1-propanol (AMP), triethanolamine, triisopropanolamine (TIPA), monoethanolamine, diethanolamine, tris[(2-hydroxy)-1-propyl]amine, 2-amino-2-methyl-1,3-propanediol (AMPD) and 2-amino-2-hydroxymethyl-1,3-propanediol, or alternatively a diamine such as lysine.

When the polycondensate contains a cationizable function of the tertiary amine type, the neutralizing agent may be an inorganic acid such as hydrochloric acid or an organic acid such as lactic acid, glycolic acid or mandelic acid. The neutralizing agent may also be an agent which quaternizes the tertiary amine function, such as, for example, alkyl halides and in particular methyl iodide or ethyl bromide. It may also be an acid salt bearing a labile halogen or a cyclic sulphonic acid ester.

A solution or an organic solvent-in-water emulsion of the polycondensate in accordance with the invention is then prepared by incorporating it into an organic, aqueous or aqueous-organic solvent system.

The organic solvents for the polycondensates of the invention which are used according to the invention are preferably chosen from acetone, methyl ethyl ketone, methyl acetate, butyl acetate, ethyl acetate, isopropanol, ethanol, dimethoxyethane, diethoxyethane, an ethylene glycol or a propylene glycol ester, an ethylene glycol or a propylene glycol ether, or an ethylene glycol or a propylene glycol ester ether, and mixtures thereof.

Depending on the type of application chosen, it is possible to use, among these solvents for the polycondensates of the invention, a solvent or a mixture of solvents which are miscible with water, one of which (which serves as diluent) evaporates before water so as to allow the polymer to be dissolved in a solvent throughout the drying of the formulation applied to the keratin substance treated. Among the water-miscible solvents, mention may be made of dimethoxyethane and a dimethoxyethane/diethoxyethane mixture. If the formulation envisaged requires the presence of water for the given application, the organic solution of the polymer may, in this case, be diluted in water in order to form an organic solvent-in-water emulsion. This emulsion may be self-stabilized by the ionic charges borne by the polycondensate, which place themselves at the interface with the water, or alternatively stabilized, if necessary, by stabilizers such as surfactants or gelling agents that are present in the aqueous phase.

It is also possible to choose a solvent or a mixture of solvents, for the polycondensates of the invention, that are immiscible with water, such as diethoxyethane. If the formulation envisaged requires the presence of water for the given application, the organic solution of the polymer may, in this case, be dispersed in water in order to form an organic solvent-in-water emulsion. This emulsion may be self-stabilized by the ionic charges borne by the polycondensate, which place themselves at the interface with the water, or stabilized, if necessary, by stabilizers such as surfactants or gelling agents present in the aqueous phase. In this case, the organic solvent or one of the organic solvents used to dissolve the polycondensate preferably has a boiling point higher than that of water. Diethyoxyethane may be used in particular.

A particularly preferred form of solvent system for the polycondensates of the invention consists in using a mixture of solvents of different polarities comprising at least one solvent (A) known as a "global" solvent for the polycondensate (for the polysiloxane blocks and the polyurethane and/or polyurea blocks) and at least one solvent (B) which is less than polar (A) and which will more specifically dissolve the polysiloxane blocks. In order to promote the stratification of the polysiloxane blocks on the deposition matrix, a solvent (B) whose rate of evaporation is slower than (A) will preferably be chosen.

Among the global solvents (A), mention may be made of acetone, methyl ethyl ketone, methyl acetate, butyl acetate, ethyl acetate, isopropanol, ethanol, dimethoxyethane, diethoxyethane, an ethylene glycol or a propylene glycol ester, an ethylene glycol or a propylene glycol ether, or an ethylene glycol or a propylene glycol ester ether, and mixtures thereof.

Among the solvents (B), mention may be made of hydrocarbons, in particular branched hydrocarbons such as isoparaffins, isodecane and cyclic silicones of the type $D_4$, $D_5$ or $D_6$.

The neutralization may be performed in situ in the solution of the polysiloxane-polyurethane/polyurea polycondensate in the solvent system by adding the determined amount of neutralizing agent.

As indicated above, the cosmetic compositions according to the invention, which thus contain, in a cosmetically acceptable support, polycondensates as defined above, have, for applications as varied as those encountered, for example, in the field of hair care or make-up or alternatively skincare, or in any other cosmetic field in which the use of a film-forming substance is desirable or sought, entirely noteworthy properties, in particular as regards their sheen and film-forming properties, their ability to retain these properties over time in the face of the action of external agents (remanence) and also as regards their properties of softness, lubrication and abrasion-resistance.

Among the applications preferably targeted by the present invention, and the various beneficial effects obtained in these applications, mention may be made more particularly of:

the field of hair products (washing, care or beauty of the hair), where the compositions according to the invention, in particular in aerosol, mousse, shampoo, conditioner, styling or treating lotion or gel, hair shaping or hair setting lacquer or lotion or alternatively fixing form, give the hair sheen, softness, ease of styling (phenomenon of "individualization" of the hair when the composition is applied), a better feel and remanence (that is to say long-lasting maintenance, even under the action of external agents) of these properties.

The field of make-up products, in particular for making up the nails and the eyelashes, where the compositions according to the invention, in nail varnish, mascara or eyeliner form, for example, afford, in the case of making up the eyelashes, the same advantages as those mentioned above for treating the hair, and, in the case of nail varnishes (where the compositions may be used as sole film-forming agents or as film-forming additive), sheen, better wettability of the nail, remanence of the film and of its sheen on washing, better abrasion-resistance (provision of a sliding effect by lubrication of the surfaces) and better rigidity.

In the field of skincare products (creams, milks, lotions, masks, sera, antisun products), where the compositions according to the invention more particularly afford sheen, better wettability and resistance to washing with water (antisun products).

The proportion of polycondensate in the cosmetic compositions (excluding nail varnishes) is generally between 0.5 and 50% and preferably between 1 and 20% by weight relative to the total weight of the composition. In the case of nail varnishes, this proportion may be up to 30% by weight.

The compositions may also, obviously, contain various adjuvants intended to make them acceptable in a particular cosmetic application.

The compositions according to the invention may contain UV-A or LTW-B or broad-band sunscreens and may thus be used as antisun products.

The compositions according to the invention may moreover contain conventional cosmetic additives chosen from fatty substances, organic solvents, silicones, thickeners, softeners, antifoaming agents, moisturizers, wetting agents, treating agents (agents for combating hair loss, antidandruff agents, etc.), anionic, nonionic or amphoteric polymers or mixtures thereof, antiperspirants, basifying agents, dyes, pigments, fragrances, preserving agents and propellants when the compositions are in aerosol form.

More precisely, an oil or a wax or mixtures thereof, fatty acids, fatty alcohols, fatty acid esters such as triglycerides of $C_6$–$C_{18}$ fatty acids, petroleum jelly, paraffin, lanolin or hydrogenated or acetylated lanolin may be used as fatty substance.

Among the oils, mention may be made of mineral, animal, plant or synthetic oils and in particular liquid petroleum jelly, liquid paraffin, castor oil, jojoba oil or sesame oil, as well as silicone oils and gums and isoparaffins.

Among the animal, fossil, plant, mineral or synthetic waxes, mention may be made in particular of beeswax, carob wax, candelilla wax, ozocerite, micro-crystalline waxes and silicone waxes and resins.

Among the thickeners, mention may be made of:

modified celluloses such as hydroxyethylcellulose, methylcellulose, hydroxypropylcellulose and carboxymethylcellulose. Among these, mention may be made in particular of the gums sold under the name "Cellosize QP 44001H" by the company Amercol, carob gum, guar gum, quaternized guar gum, sold under the name "Jaguar C-13-S" by the company Meyhall, hydroxypropyl guar gum, xanthan gum, crosslinked polyacrylic acids such as the "Carbopols" from the company Goodrich, the polyglyceryl (meth)acrylate polymers sold under the names "Hispagel" or "Lubragel" by the companies Hispano Quimica and Guardian, polyvinylpyrrolidone, polyvinyl alcohol, crosslinked acrylamide polymers and copolymers, such as those sold under the names "PAS 5161" or "Bozepol C" by the company Hoechst, "Sepigel 305" by the company Seppic or "Salcare SC95" by the company Allied Colloid, or alternatively crosslinked homopolymers of methacrylolyloxyethyltrimethylammonium chloride, sold under the name "Salcare SC95" by the company Allied Colloid.

Several examples of the preparation of polysiloxane-polyurethane polycondensates and of their solutions or emulsions and of cosmetic compositions containing them will now be given by way of illustration of the invention.

The syntheses leading to the polysiloxane-polyurethane multiblock polycondensates were carried out starting with prepolymers of the α,ω-hydroxyorgano-functional polydimethylsiloxane type (commercial products sold by the company Goldschmidt under the names Tegomer H-Si 2111 and Tegomer H-Si 2311) of structure:

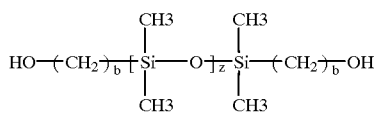

and also having the characteristics collated in the table below:

| Functional groups | Primary hydroxyl groups | |
|---|---|---|
| Commercial name | Tegomer H-Si 2111 | Tegomer H-Si 2311 |
| Functionality | 2 | 2 |
| Number of units z | about 10 | about 30 |
| Hydroxyl number (mg KOH/g) | 120 (±10) | 45 (±5) |
| Viscosity at 25° C. (cP) | 85 (±10) | 115 (±15) |
| Number-average molecular weight (Mn) | 700 | 2200 |

These two commercial products will be referred to hereinbelow for convenience as SIL 700 and SIL 2200 (name based on their respective molecular weights).

EXAMPLE 1

In this example, an anionizable polysiloxane-polyurethane polycondensate was prepared, of theoretical structure:

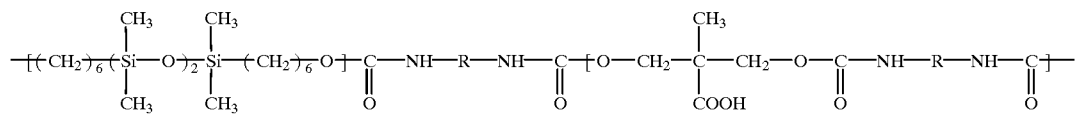

in which R represents:

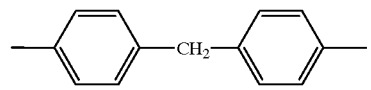

and corresponding to the reaction between:
  1 mol of SIL 700 (polysiloxane prepolymer)
  2 mol of 4,4'-diphenylmethane diisocyanate (referred to hereinbelow as MDI)
  and 1 mol of dimethylolpropionic acid (coupler, referred to hereinbelow as DMPA), these values being relative to 1 mol of SIL 700.

50 g of MDI and 50 g of tetrahydrofuran (THF) are introduced, under a stream of nitrogen, into a cylindrical reactor fitted with a central stirrer of the anchor-paddle type, a thermometer, a condenser and an inlet for bubbling nitrogen through, and mounted with a dropping funnel. The mixture is dissolved with stirring and at room temperature.

Simultaneously, 70 g of SIL 700 are dissolved in 70 g of THF and the solution thus obtained is poured into the dropping funnel located above the reactor.

This solution of SIL 700 is then introduced, with stirring and under a stream of nitrogen, into the reactor containing the solution of MDI, while maintaining the temperature of the reaction medium at 50° C. by external heating.

The introduction of the SIL 700 solution lasts 1 h 30 and the temperature of the reaction medium is maintained at 50° C. throughout the introduction.

After the solution has been introduced, the reaction leads to the quantitative formation of a polysiloxane prepolymer containing α,ω-diisocyanate ends.

A solution of DMPA obtained by dissolving 13.4 g of DMPA in 400 g of THF is then introduced (introduction time: 30 min) into the reactor containing the above prepolymer, still with stirring, bubbling with nitrogen and maintenance of the temperature at 50° C. At the start of the introduction, 0.15 g of dibutyltin dilaurate which serves as catalyst is also introduced into the reaction medium. The whole is then left to react for 10 h, with stirring and at 50° C.

The end of the reaction may be monitored by checking, by infrared analysis, the absence of —N=C=O absorption bands at 2270 cm$^{-1}$. If needed, ethanol may also be added to the reaction medium in order to quench the reaction and totally consume the —N=C=O groups that are still available; in this case, it is possible, for example, to add about 10 ml of ethanol and leave the whole to react for a further 4 h at 50° C.

At the end of the reaction, an organic (THF) solution of the desired polycondensate is obtained, which is then recovered and purified by precipitation of the said solution in 5 l of an equi-volume (50/50) petroleum ether/ethyl ether mixture. The recovery yield is 90% by weight after drying.

The acid number of the polycondensate obtained is 46 (theoretical: 42).

Its number-average molecular weight is 5000.

The polymer obtained is soluble in solvents such as dimethoxyethane, ethanol, isododecane and ethyl acetate.

EXAMPLE 2

An anionizable polysiloxane-polyurethane polycondensate of the same theoretical structure as that of Example 1, but this time obtained from the polysiloxane prepolymer SIL 2200, is prepared here.

The procedure followed is thus identical to that of Example 1, but the amounts of reactants used are this time as follows:
80 g of SIL 2200 dissolved in 80 g of THF
18.2 g of MDI dissolved in 20 g of THF
4.9 g of DMPA dissolved in 200 g of THF
0.1 g of dibutyltin dilaurate in order, here also, to abide by the proportions 1 mol of SIL 2200: 2 mol of MDI: 1 mol of DMPA.

In addition, the recovery and purification of the desired final polycondensate takes place this time more simply by precipitation of the organic solution containing it in 5 l of deionized water.

The recovery yield is, in this case, 92% by weight.

The acid number of the polycondensate obtained is 21.7 (theoretical: 19.8).

Its number-average molecular weight is 6300.

The polymer obtained is soluble in solvents such as dimethoxyethane, ethanol, isododecane and ethyl acetate.

EXAMPLE 3

In this example, a cationizable polysiloxane-polyurethane polycondensate was prepared, of theoretical structure:

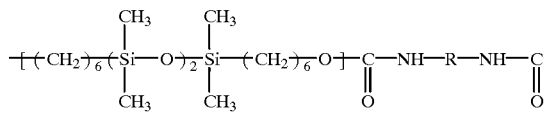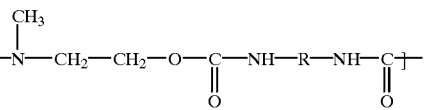

in which R represents:

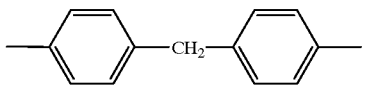

and corresponding to the reaction between:
1 mol of SIL 700
2 mol of MDI
1 mol of N-methyldiethanolamine (coupler, referred to hereinbelow as MEA) these values being relative to 1 mol of SIL 700.

50 g of MDI and 50 g of THF are introduced, under a stream of nitrogen, into the same reactor as that of Example 1, equipped in the same way. Dissolution of the mixture takes place with stirring and at room temperature.

In parallel, 70 g of SIL 700 are dissolved in 70 g of THF and the solution thus obtained is poured into the dropping funnel located above the reactor.

This solution of SIL 700 is then introduced, with stirring and under a stream of nitrogen, into the reactor containing the solution of MDI, while maintaining the temperature of the reaction medium at 50° C. by external heating.

The introduction of the SIL 700 solution lasts 1 h 30 and the temperature of the reaction medium is maintained at 50° C. throughout the introduction.

After the introduction, the reaction medium is diluted with 350 g of THF, while maintaining the temperature at 50° C. The reaction leads to the quantitative formation of a polysiloxane prepolymer containing α,ω-diisocyanate ends.

A solution of MEA obtained by dissolving 12.5 g of MEA in 70 g of THF is then introduced (introduction time: 30 min) into the reactor containing the above prepolymer, still with stirring, bubbling with nitrogen and maintenance of the temperature at 50° C. The whole is then left to react for 7 h with stirring and at 50° C.

The end of the reaction may be monitored by checking, by infrared analysis, the absence of —N=C=O absorption bands at 2270 cm$^{-1}$. If needed, ethanol may also be added to the reaction medium in order to quench the reaction and totally consume the —N=C=O groups that are still available; in this case, it is possible, for example, to add about 10 ml of ethanol and leave the whole to react for a further 4 h at 50° C.

At the end of the reaction, an organic (THF) solution of the desired polycondensate is obtained, which is then recovered and purified by precipitation of the said solution in 5 l of an equi-volume (50/50) petroleum ether/ethyl ether mixture. The recovery yield is 93% by weight after drying.

The acid number of the polycondensate obtained is 45.7 (theoretical: 43).

Its number-average molecular weight is 12,600.

The polymer obtained is soluble in solvents such as dimethoxyethane, ethanol, isododecane and ethyl acetate.

EXAMPLE 4

Three examples of hair formulations are given here.

Hair Shaping Lotion

| | |
|---|---|
| Polymer of Example 1 | 2 g |
| Dimethoxyethane | 50 g |
| AMP | 0.146 g |
| Ethanol | 40.67 g |
| Isododecane | 7.18 g |

This lotion is obtained by dissolving the polymer in the dimethoxyethane and then adding the neutralizing agent, after which the solution is diluted by adding ethanol and isododecane.

When applied to the hair after shampooing, this composition affords good hold of the hairstyle and hair with very good sheen.

Hair Shaping Lotion

| | |
|---|---|
| Polymer of Example 2 | 2 g |
| Dimethoxyethane | 50 g |
| AMP | 0.069 g |
| Ethanol | 43.14 g |
| Isododecane | 4.80 g |

This lotion is obtained by dissolving the polymer in the dimethoxyethane and then adding the neutralizing agent, after which the solution is diluted by adding ethanol and isododecane.

When applied to the hair after shampooing, this composition affords good hold of the hairstyle and hair with very good sheen.

Hair Shaping Lotion

| | |
|---|---|
| Polymer of Example 3 | 4.2 g |
| Dimethoxyethane | 47.66 g |
| Ethanol | 42.90 g |
| Isododecane | 4.76 g |
| 2M HCl solution | 0.476 g |

This lotion is obtained by dissolving the polymer in the dimethoxyethane, followed by diluting the solution by adding ethanol and isododecane. The HCl solution is then added in order to neutralize the final solution.

When applied to the hair after shampooing, this composition affords good hold of the hairstyle and hair with very good sheen.

EXAMPLE 5

Four examples of nail care bases are given here.

Nail Care Base

| | |
|---|---|
| Polymer of Example 1 | 30 g |
| Ethyl acetate | 70 g |

Nail Care Base

| | |
|---|---|
| Polymer of Example 1 | 30 g |
| Ethyl acetate | 66.5 g |
| Isododecane | 3.5 g |

Nail Care Base

| | |
|---|---|
| Polymer of Example 2 | 30 g |
| Ethyl acetate | 70 g |

Nail Care Base

| | |
|---|---|
| Polymer of Example 2 | 30 g |
| Ethyl acetate | 66.5 g |
| Isododecane | 3.5 g |

What is claimed is:

1. A composition comprising at least one solution or at least one organic solvent-in-water emulsion, wherein said at least one solution or at least one organic solvent-in-water emulsion comprises at least one multiblock polycondensate dissolved in an aqueous solvent, an organic solvent, or a mixture thereof, the chain of said at least one multiblock polycondensate comprising the repetition of at least one polysiloxane block and at least one second block, wherein said at least one second block is chosen from polyurethane and polyurea blocks, wherein said at least one second block comprises at least one ionizable group, wherein said at least one second block is chosen from at least one polyurethane and/or polyurea block of formula (II) below:

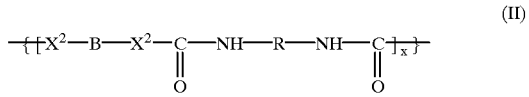

(II)

wherein $X^2$, which may be identical or different, is —O— or —NH—,

R is a divalent radical wherein said divalent radical is an aromatic, aliphatic or cycloaliphatic radical, x is an interger ranging from 1 to 10, and B is chosen from radicals of formula (III):

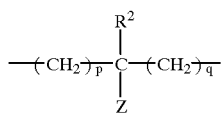
(III)

wherein
$R^2$ is a linear or branched $C_1$–$C_3$ alkyl radical,
Z is a —COOH or —$SO_3$H function or a salt of these acidic functions, and
p and q, which may be identical or different, are integers ranging from 1 to 5, or formula (III'):

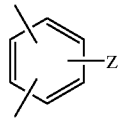
(III')

wherein
Z is a —COOH or —$SO_3$H function or a salt of these acidic functions, and further wherein the composition is a cosmetic or dermatological composition, and wherein the numerical ratio between said at least one polyurethane and/or polyurea block and said at least one polysiloxane block in the polycondensate ranges from 1:1 to 10:1.

2. A composition according to claim 1 wherein said ratio ranges from 1:1 to 3:1.

3. A process for treating a keratin substance comprising applying a composition comprising at least one solution or at least one organic solvent-in-water emulsion to said substance, wherein said at least one solution or at least one organic solvent-in-water emulsion comprises at least one multiblock polycondensate dissolved in an aqueous solvent, an organic solvent, or a mixture thereof, the chain of said at least one multiblock polycondensate comprising the repetition of at least one polysiloxane block and at least one second block, wherein if said at least one second block is chosen from polyurethane and polyurea blocks, and further wherein said at least one second block comprises at least one ionizable group.

4. A process according to claim 3, wherein the number-average molecular weight of said polycondensate ranges from 2000 to 500,000.

5. A process according to claim 4, wherein said molecular weight ranges from 3000 to 250,000.

6. A process according to claim 3, wherein the numerical ratio between said at least one polyurethane and/or polyurea block and said at least one polysiloxane block in the polycondensate ranges from 1:1 to 10:1.

7. A process according to claim 6, wherein said ratio ranges from 1:1 to 3:1.

8. A process according to claim 3, wherein said at least one ionizable group is a carboxylic function, a sulphonic function, or a combination of carboxylic and sulphonic functions, said carboxylic function, said sulphonic function, or said combination being in free or partially neutralized or totally neutralized form.

9. A process according to claim 3, wherein said at least one ionizable group is a tertiary amine which is either non-neutralized or totally or partially neutralized or quaternized, or a combination thereof.

10. A process according to claim 9, wherein the degree of neutralization or of quaternization of said tertiary amines ranges from 0 to 100%.

11. A process according to claim 10, wherein said degree ranges from 10 to 100%.

12. A process according to claim 3, wherein said at least one polysiloxane block is of the formula (I) below:

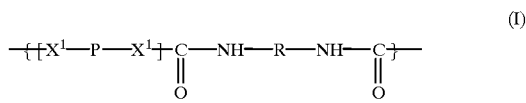
(I)

wherein:
P is a polysiloxane segment,
$X^1$, which may be identical or different, is —O— or —NH—, and
R is a divalent radical wherein said divalent radical is an aromatic, aliphatic or cycloaliphatic radical.

13. A process according to claim 12, wherein said polysiloxane segment P is of the formula (I') below:

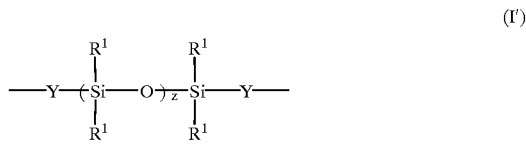
(I')

wherein:
the radicals $R^1$, which may be identical or different, are aromatic radicals or monovalent $C_1$–$C_{20}$ hydrocarbon radicals which are free or substantially free of ethylenic unsaturations,
Y represents a divalent hydrocarbon radical, and
z is an integer such that the average molecular weight of the polysiloxane segment ranges from 300 to 10,000.

14. A process according to claim 13, wherein said divalent hydrocarbon radical Y is an alkylene radical of formula —$(CH_2)_3$—, wherein a represents an integer ranging/from 1 to 10.

15. A process according to claim 13, wherein said radicals $R^1$ are alkyl radicals, cycloalkyl radicals, aryl radicals, or arylalkyl radicals.

16. A process according to claim 15, wherein said alkyl radicals are methyl, ethyl, propyl, isopropyl, butyl, pentyl, hexyl, octyl, decyl, dodecyl or octadecyl radicals.

17. A process according to claim 15, wherein said cycloalkyl radicals are cyclohexyl radicals.

18. A process according to claim 15, wherein said aryl radicals are phenyl, naphthyl, tolyl or xylyl radicals.

19. A process according to claim 15, wherein said arylalkyl radicals are benzyl and phenylethyl radicals.

20. A process according to claim 12, wherein said polysiloxane segment P is of the formula (I") below:

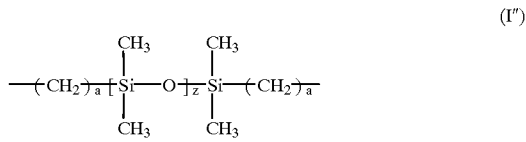
(I")

wherein a represents an integer ranging from 1 to 10, and z represents an integer such that the average molecular weight of the polysiloxane segment ranges from 300 to 10,000.

21. A process according to claim 3, wherein said at least one polyurethane and/or polyurea block is of the formula (II) below:

$$-\{[X^2-B-X^2-\underset{O}{\overset{\|}{C}}-NH-R-NH-\underset{O}{\overset{\|}{C}}]_x\}-\qquad (II)$$

wherein:

- $X^2$, which may be identical or different, is —O— or —NH—,
- R is a divalent radical wherein said divalent radical is an aromatic, aliphatic or cycloaliphatic radical,
- x is an integer ranging from 1 to 10, and
- B is a divalent hydrocarbon radical bearing a positive or negative ionic charge.

22. A process according to claim 21, wherein x ranges from 1 to 3.

23. A process according to claim 21, wherein said radical B bears a group having at least one carboxylic function, at least one sulphonic function or a combination of carboxylic and sulphonic functions, wherein said at least one carboxylic function, said at least one sulphonic function or said combination is in free form or alternatively partially or totally neutralized with an inorganic or organic base.

24. A process according to claim 23, wherein said radical B is of the formula (III) below:

$$-(CH_2)_p-\underset{Z}{\overset{R^2}{\underset{|}{C}}}-(CH_2)_q-\qquad (III)$$

wherein $R^2$ is a linear or branched $C_1$–$C_3$ alkyl radical, Z is a —COOH or —SO$_3$H function or a salt of these acidic functions, and p and q, which may be identical or different, are integers ranging from 1 to 5.

25. A process according to claim 23, wherein said radical B is of the formula (III') below:

(III')

wherein Z is a —COOH or —SO$_3$H function or a salt of these acidic functions.

26. A process according to claim 21, wherein said radical B bears tertiary amine groups, and further wherein said tertiary amine groups are either non-neutralized or partially or totally neutralized with an inorganic or organic base, or quaternized.

27. A process according to claim 26, wherein said radical B is of the formula (IV) below:

$$-(CH_2)_r-\underset{R^3}{\overset{|}{N}}-(CH_2)_s-\qquad (IV)$$

wherein $R^3$ is a linear or branched $C_1$–$C_4$ alkyl radical, and r and s, which may be identical or different, are both integers which range from 1 to 10.

28. A process according to claim 27, wherein the radical B, in neutralized or quaternized form, is of the formula (IV'):

$$-(CH_2)_r-\underset{R^3}{\overset{R^4}{\underset{|}{\overset{|}{N^+}}}}-(CH_2)_s-\qquad (IV')$$

wherein $R^3$ is as defined in claim 27, and $R^4$ is either hydrogen or a linear or branched $C_1$–$C_{10}$ alkyl radical or an aromatic ring.

29. A process according to claim 12, wherein said radical R is a radical of the following formulae:

wherein b is an integer ranging from 0 to 3, and c is an integer ranging from 1 to 20.

30. A process according to claim 29, wherein c ranges from 2 to 12.

31. A process according to claim 29, wherein said radical R is hexamethylene, 4,4'-biphenylenemethane, 2,4-tolylene, 2,6-tolylene, 1,5-naphthylene, p-phenylene, methylene4,4-bis-cyclohexyl or the divalent radical derived from isophorone.

32. A process according to claim 3, wherein said polycondensate is obtained according to a process comprising the steps of (A) in a first step, reacting a polysiloxane polymer of α,ω-dihydroxypolysiloxane, α,ω-diaminopolysiloxane, α,ω-aminohydroxy- or hydroxyaminopolysiloxane type, and a diisocyanate, wherein said diisocyanate is present in stoichiometric amount or in stoichiometric excess and further wherein a polysiloxane is obtained having an isocyanate function at each of its chain ends;

(B) in a second step, coupling the chains of the polysiloxane obtained in said first step by reaction with a coupler wherein said coupler is a diol, daimine, or aminoalcohol, and further wherein said coupler bears cationizable or anionizable groups; and (C) in a third step, optionally partially or totally ionizing the cationizable or anionizable groups of the polycondensate obtained after the second step, and dissolving the polycondensate in an aqueous, organic or aqueous-organic solvent system.

33. A process according to claim 32, wherein the degree of ionization in said third step ranges from 0 to 100%.

34. A process according to claim 33, wherein said degree of ionization ranges from 10 to 100%.

35. A process according to claim 32, wherein the starting polysiloxane polymer in said first step is of the formula:

wherein P is a polysiloxane segment, and $X^3$, which can be identical or different, is —OH or —NH$_2$.

36. A process according to claim 32, wherein said diisocyanate is of the formula:

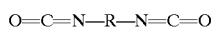

wherein R is a divalent radical chosen from aromatic, aliphatic and cycloaliphatic radicals.

37. A process according to claim 32, wherein said coupler is of the formula:

wherein B is a divalent hydrocarbon radical bearing a positive or negative ionic charge, and $X^4$ is —OH or —NH$_2$.

38. A process according to claim 3, wherein said solvent system comprises at least one organic solvent chosen from acetone, methyl ethyl ketone, methyl acetate, butyl acetate, ethyl acetate, isopropanol, ethanol, dimethoxyethane, diethoxyethane, ethylene glycol and propylene glycol esters, ethylene glycol and propylene glycol ethers, ethylene glycol, and propylene glycol ester ethers.

39. A process according to claim 38, wherein said at least one organic solvent is miscible with water.

40. A process according to claim 3 wherein said solvent system contains at least one organic solvent which is immiscible in water.

41. A process according to claim 3, wherein said solvent system contains at least one global solvent for the polycondensate and at least one additional solvent which is less polar than said global solvent.

42. A process according to claim 41, wherein said at least one additional solvent dissolves the polysiloxane blocks of the polycondensate and has a slower rate of evaporation than said global solvent.

43. A process according to claim 41, wherein said at least one global solvent is acetone, methyl ethyl ketone, methyl acetate, butyl acetate, ethyl acetate, isopropanol, ethanol, dimethoxyethane, diethoxyethane, ethylene glycol or propylene glycol esters, ethylene glycol or propylene glycol ethers, or ethylene glycol or propylene glycol ester ethers or a mixture thereof.

44. A process according to claim 41, wherein said at least one additional solvent is a cyclic silicone, a hydrocarbon, or a mixture thereof.

45. A process according to claim 3, wherein said composition is a hair composition.

46. A process according to claim 3, wherein said composition is a make-up composition.

47. A process according to claim 3, wherein said composition is a nail varnish or a nail care base.

48. A process according to claim 3, wherein said composition is a mascara.

49. A process according to claim 3, wherein said composition is a skincare composition.

50. A process according to claim 3, wherein said composition is an antisun composition.

51. A composition comprising at least one solution or at least one organic solvent-in-water emulsion, wherein said at least one solution or at least one organic solvent-in-water emulsion comprises at least one multiblock polycondensate dissolved in an aqueous solvent, an organic solvent, or a mixture thereof, the chain of said at least one multiblock polycondensate comprising the repetition of at least one polysiloxane block and at least one second block, wherein said at least one second block is chosen from polyurethane and polyurea blocks, wherein said at least one second block comprises at least one ionizable group, wherein said at least one second block is chosen from at least one polyurethane and/or polyurea block of formula (II) below:

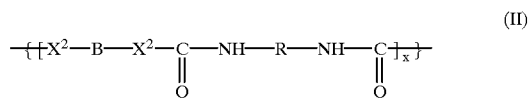

wherein
$X^2$, which may be identical or different, is —O— or —NH—,
R is a divalent radical wherein said divalent radical is an aromatic, aliphatic or cycloaliphatic radical,
x is an interger ranging from 1 to 10, and
B is chosen from radicals of formula (III):

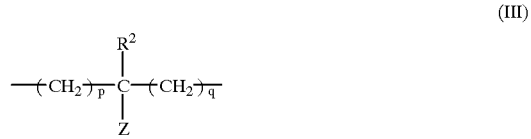

wherein
$R^2$ is a linear or branched $C_1$–$C_3$ alkyl radical,
Z is a —COOH or —SO$_3$H function or a salt of these acidic functions, and
p and q, which may be identical or different, are integers ranging from 1 to 5, or formula (III'):

wherein
Z is a —COOH or —SO$_3$H function or a salt of these acidic functions, and further wherein the composition is a cosmetic or dermatological composition, and wherein the composition contains at least one organic solvent which is immiscible in water.

52. A composition comprising at least one solution or at least one organic solvent-in-water emulsion, wherein said at least one solution or at least one organic solvent-in-water emulsion comprises at least one multiblock polycondensate dissolved in an aqueous solvent, an organic solvent, or a mixture thereof, the chain of said at least one multiblock polycondensate comprising the repetition of at least one polysiloxane block and at least one second block, wherein said at least one second block is chosen from polyurethane and polyurea blocks, wherein said at least one second block comprises at least one ionizable group, wherein said at least one second block is chosen from at least one polyurethane and/or polyurea block of formula (II) below:

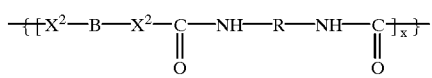

(II)

wherein $X^2$, which may be identical or different, is —O— or —NH—,

R is a divalent radical wherein said divalent radical is an aromatic, aliphatic or cycloaliphatic radical, x is an interger ranging from 1 to 10, and B is chosen from radicals of formula (III):

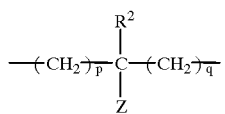

(III)

wherein $R^2$ is a linear or branched $C_1$–$C_3$ alkyl radical,

Z is a —COOH or —SO$_3$H function or a salt of these acidic functions, and p and q, which may be identical or different, are integers ranging from 1 to 5, or formula (III'):

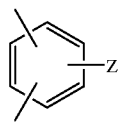

(III')

wherein

Z is a —COOH or —SO$_3$H function or a salt of these acidic functions, and further wherein the composition is a cosmetic or dermatological composition, wherein the composition contains at least one global solvent for the polycondensate and at least one additional solvent which is less polar than said global solvent, and wherein said at least one additional solvent dissolves the polysiloxane blocks of the polycondensate and has a slower rate of evaporation than said global solvent.

53. A composition comprising at least one solution or at least one organic solvent-in-water emulsion, wherein said at least one solution or at least one organic solvent-in-water emulsion comprises at least one multiblock polycondensate dissolved in an aqueous solvent, an organic solvent, or a mixture thereof, the chain of said at least one multiblock polycondensate comprising the repetition of at least one polysiloxane block and at least one second block, wherein said at least one second block is chosen from polyurethane and polyurea blocks, wherein said at least one second block comprises at least one ionizable group, wherein said at least one second block is chosen from at least one polyurethane and/or polyurea block of formula (II) below:

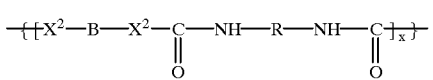

(II)

wherein $X^2$, which may be identical or different, is —O— or —NH—,

R is a divalent radical wherein said divalent radical is an aromatic, aliphatic or cycloaliphatic radical, x is an interger ranging from 1 to 10, and B is chosen from radicals of formula (III):

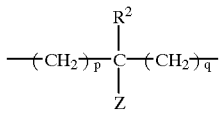

(III)

wherein $R^2$ is a linear or branched $C_1$–$C_3$ alkyl radical,

Z is a —COOH or —SO$_3$H function or a salt of these acidic functions, and p and q, which may be identical or different, are integers ranging from 1 to 5, or formula (III'):

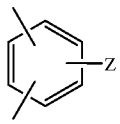

(III')

wherein

Z is a —COOH or —SO$_3$H function or a salt of these acidic functions, and further wherein the composition is a cosmetic or dermatological composition, wherein the composition contains at least one global solvent for the polycondensate and at least one additional solvent which is less polar than said global solvent, and wherein said at least one additional solvent is selected from cyclic silicones and hydrocarbons.

54. A process for preparing a cosmetic composition, said process comprising adding at least one polycondensate solution or emulsion as a film-forming agent or as an additive for a film-forming agent, to the composition, wherein said at least one polycondensate solution or emulsion comprises at least one solution or at least one organic solvent-in-water emulsion, wherein said at least one solution or at least one organic solvent-in-water emulsion comprises at least one multiblock polycondensate dissolved in an aqueous solvent, an organic solvent, or a mixture thereof, the chain of said at least one multiblock polycondensate comprising the repetition of at least one polysiloxane block and at least one second block, wherein said at least one second block is chosen from polyurethane and polyurea blocks, wherein said at least one second block comprises at least one ionizable group, wherein said at least one second block is chosen from at least one polyurethane and/or polyurea block of formula (II) below:

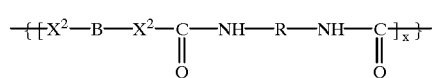 (II)

wherein

X$^2$, which may be identical or different, is —O— or —NH—,

R is a divalent radical wherein said divalent radical is an aromatic, aliphatic or cycloaliphatic radical, x is an interger ranging from 1 to 10, and B is chosen from radicals of formula (III):

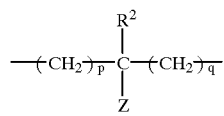 (III)

wherein

R$^2$ is a linear or branched C$_1$–C$_3$ alkyl radical,

Z is a —COOH or —SO$_3$H function or a salt of these acidic functions, and p and q, which may be identical or different, are integers ranging from 1 to 5, or formula (III'):

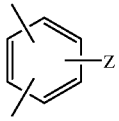 (III')

wherein

Z is a —COOH or —SO$_3$H function or a salt of these acidic functions, and further wherein the composition is a cosmetic or dermatological composition.

* * * * *

UNITED STATES PATENT AND TRADEMARK OFFICE
CERTIFICATE OF CORRECTION

PATENT NO. : 6,395,265 B1
DATED : May 28, 2002
INVENTOR(S) : Nathalie Mougin et al.

It is certified that error appears in the above-identified patent and that said Letters Patent is hereby corrected as shown below:

Title page,
Item [57], ABSTRACT,
Lines 1-2, delete "Cosmetic compositions based on multiblock ionizable polycondensates, and uses thereof".

Column 16,
Line 67, "interger" should read -- integer --.

Column 17,
Line 43, after "wherein", delete "if".

Column 18,
Line 41, "-$(CH_2)_3$-," should read -- -$(CH_2)_a$-, --; and "ranging/from" should read -- ranging from --.

Column 20,
Lines 46-47, "methylene4,4-bis-cyclohexyl" should read -- methylene-4,4-bis-cyclohexyl --.
Line 62, "daimine," should read -- diamine, --.

Column 22,
Line 25, "interger" should read -- integer --.

Column 23,
Line 16, "interger" should read -- integer --.

Column 24,
Line 13, "interger" should read -- integer --.

UNITED STATES PATENT AND TRADEMARK OFFICE
CERTIFICATE OF CORRECTION

PATENT NO. : 6,395,265 B1
DATED : May 28, 2002
INVENTOR(S) : Nathalie Mougin et al.

It is certified that error appears in the above-identified patent and that said Letters Patent is hereby corrected as shown below:

<u>Column 25,</u>
Line 13, "interger" should read -- integer --.

Signed and Sealed this

Fifteenth Day of October, 2002

*Attest:*

*Attesting Officer*

JAMES E. ROGAN
*Director of the United States Patent and Trademark Office*